(12) United States Patent
Venkatraman et al.

(10) Patent No.: US 10,188,345 B2
(45) Date of Patent: Jan. 29, 2019

(54) METHOD AND APPARATUS FOR PROVIDING BIOFEEDBACK DURING MEDITATION EXERCISE

(71) Applicant: Fitbit, Inc., San Francisco, CA (US)

(72) Inventors: Subramaniam Venkatraman, Walnut Creek, CA (US); Alexandros Pantelopoulos, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 38 days.

(21) Appl. No.: 15/043,330

(22) Filed: Feb. 12, 2016

(65) Prior Publication Data
US 2016/0166197 A1 Jun. 16, 2016

(51) Int. Cl.
*A61B 5/00* (2006.01)
*A61B 5/11* (2006.01)
(Continued)

(52) U.S. Cl.
CPC ............. *A61B 5/486* (2013.01); *A61B 5/021* (2013.01); *A61B 5/0205* (2013.01);
(Continued)

(58) Field of Classification Search
CPC ..... A61B 5/02405; A61B 5/486; A61B 5/118; A61B 5/0205; A61B 5/7271;
(Continued)

(56) References Cited

U.S. PATENT DOCUMENTS 6,081,742 A * 6/2000 Amano ................ A61B 5/0205
600/484
8,684,900 B2 4/2014 Tran
(Continued)

FOREIGN PATENT DOCUMENTS

WO WO 12/170586 12/2012
WO WO 12/170924 12/2012
(Continued)

OTHER PUBLICATIONS

HeartMath, Inc., 2016, Minimize stress in just minutes a day, http://heartmath.com, 3 pp.
(Continued)

*Primary Examiner* — Jack Yip
(74) *Attorney, Agent, or Firm* — Knobbe, Martens, Olson & Bear, LLP

(57) ABSTRACT

A method and apparatus for providing biofeedback during a meditation exercise are disclosed. In one aspect, the wearable device includes one or more biometric sensors and a user interface. The method may involve prompting the user, via the user interface, to perform a meditation exercise, the meditation exercise being associated with a target physiological metric related to the physiology of the user. The method may involve measuring, based on output of at least one of the one or more biometric sensors, a physiological metric of the user during the meditation exercise. The method may involve determining a performance score indicating the user's performance during the meditation exercise based on comparing the measured physiological metric with the target physiological metric. The method may involve providing, via the user interface, based on the performance score, feedback information indicative of the user's performance during the meditation exercise.

29 Claims, 15 Drawing Sheets

(51) Int. Cl.
*A61B 5/024* (2006.01)
*A61B 5/08* (2006.01)
*A61B 5/021* (2006.01)
*A61B 5/16* (2006.01)
*A61B 5/0205* (2006.01)
*A61B 5/145* (2006.01)
*A61B 5/0488* (2006.01)
*A61B 5/0476* (2006.01)

(52) U.S. Cl.
CPC ........ *A61B 5/02405* (2013.01); *A61B 5/0816* (2013.01); *A61B 5/11* (2013.01); *A61B 5/16* (2013.01); *A61B 5/681* (2013.01); *A61B 5/7246* (2013.01); *A61B 5/7271* (2013.01); *A61B 5/7435* (2013.01); *A61B 5/0022* (2013.01); *A61B 5/0059* (2013.01); *A61B 5/02055* (2013.01); *A61B 5/0476* (2013.01); *A61B 5/0488* (2013.01); *A61B 5/14532* (2013.01); *A61B 5/14542* (2013.01); *A61B 5/742* (2013.01); *A61B 5/7405* (2013.01); *A61B 5/7455* (2013.01)

(58) Field of Classification Search
CPC ..... A61B 5/7246; A61B 5/742; A61B 5/7405; A61B 5/7455; A61B 5/0022; A61B 5/02055; A61B 5/11; A61B 5/0059; A61B 5/14532; A61B 5/14542; A61B 5/0488; A61B 5/0476; A61B 5/0816; A61B 5/021; A61B 5/7435; A61B 5/16; A61B 5/681; G06F 19/3481; A61N 1/36592; A63B 2024/0068
USPC ........ 600/301, 300, 513, 595; 434/247, 236; 482/1, 8; 702/19; 340/575
See application file for complete search history.

(56) References Cited

U.S. PATENT DOCUMENTS

| | | | |
|---|---|---|---|
| 8,764,651 B2 | 7/2014 | Tran | |
| 2008/0287751 A1 | 11/2008 | Stivoric et al. | |
| 2010/0174205 A1* | 7/2010 | Wegerif | A61B 5/02405 600/515 |
| 2010/0240945 A1* | 9/2010 | Bikko | A61B 5/02405 600/28 |
| 2011/0015468 A1* | 1/2011 | Aarts | A61B 5/0205 600/26 |
| 2012/0116684 A1* | 5/2012 | Ingrassia, Jr. | G06F 19/321 702/19 |
| 2013/0203475 A1* | 8/2013 | Kil | G06Q 10/101 463/7 |
| 2013/0274830 A1* | 10/2013 | Skelton | A61N 1/36128 607/62 |
| 2014/0180022 A1 | 6/2014 | Stivoric et al. | |
| 2014/0197947 A1* | 7/2014 | Bahorich | G06F 19/3418 340/539.12 |
| 2014/0358012 A1* | 12/2014 | Richards | A61B 5/02438 600/479 |
| 2015/0026647 A1 | 1/2015 | Park et al. | |
| 2015/0342518 A1* | 12/2015 | Persidsky | A61B 5/486 600/534 |
| 2016/0058329 A1* | 3/2016 | Srinivas | A61B 5/0205 600/595 |

FOREIGN PATENT DOCUMENTS

| | | |
|---|---|---|
| WO | WO 12/171032 | 12/2012 |
| WO | WO 15/127067 | 8/2015 |
| WO | WO 16/003269 | 1/2016 |

OTHER PUBLICATIONS

MIT CSAIL, Jun. 2015, Video Magnification, http://people.csail.mit.edu/mrub/vidmag, 4 pp.

* cited by examiner

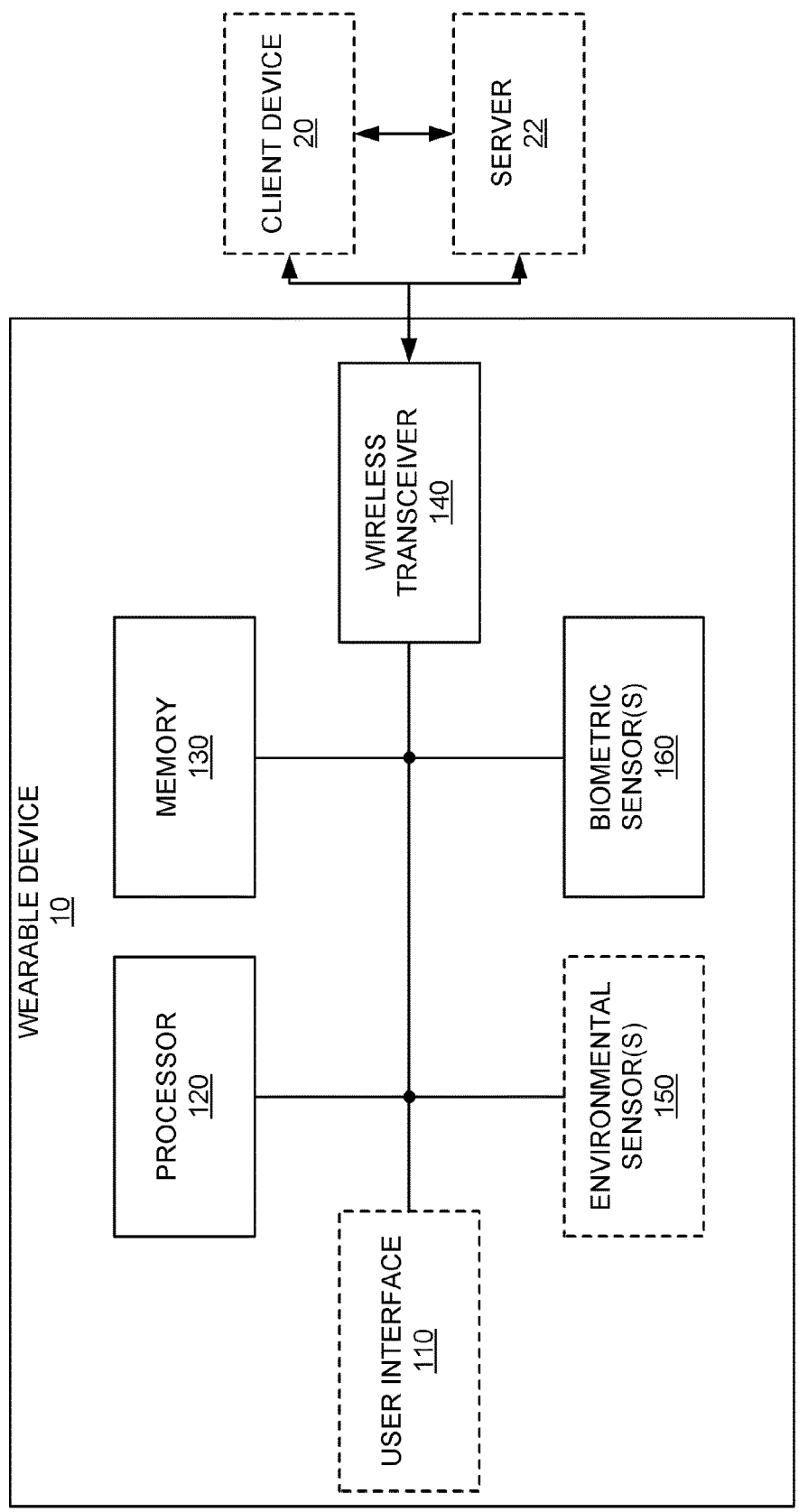

HR line   Bar   Flower

Lotus   Zen Rocks   Zen Line

Bonzai    Stand to sit

Good

METHOD AND APPARATUS FOR PROVIDING BIOFEEDBACK DURING MEDITATION EXERCISE

TECHNICAL FIELD

This disclosure relates to the field of wearable devices, and particularly to providing biofeedback, via wearable devices, during a meditation or relaxation exercise (e.g., a breathing exercise).

BACKGROUND

Consumer interest in personal health has led to a variety of personal health monitoring devices being offered on the market. Such devices, until recently, tended to be complicated to use and were typically designed for use with one activity, for example, bicycle trip computers.

Advances in sensors, electronics, and power source miniaturization have allowed the size of personal health monitoring devices, also referred to herein as "biometric tracking," "biometric monitoring," or simply "wearable" devices, to be offered in extremely small sizes that were previously impractical. The number of applications for these devices is increasing as the processing power and component miniaturization for wearable devices improves.

SUMMARY

The systems, methods and devices of this disclosure each have several innovative aspects, no single one of which is solely responsible for the desirable attributes disclosed herein.

In one aspect, there is provided a method of operating a wearable device, the wearable device comprising one or more biometric sensors and a user interface, the biometric sensors including a motion sensor. The method may involve: determining, based on output of the motion sensor, that a user's movements are within a tolerance range for movement; and prompting the user, via the user interface, to perform a meditation or relaxation exercise (e.g., a breathing exercise) in response to determining that the user's movements are within the tolerance range for movement, the meditation exercise being associated with a target physiological metric (e.g., a target respiration metric). The method may further involve: measuring, based on output of at least one of the one or more biometric sensors, a physiological metric of the user (e.g., a respiration metric of the user's breathing pattern) during the meditation exercise; and determining a performance score indicating the user's performance during the meditation exercise based at least in part on comparing the measured physiological metric with the target physiological metric. The method may further involve providing, via the user interface, based on the determined performance score, feedback information indicative of the user's performance during the meditation exercise.

In another aspect, there is provided a method of operating a wearable device, the wearable device comprising one or more biometric sensors and a wireless communication transceiver, the biometric sensors including a motion sensor. The method may involve: determining, based on output of the motion sensor, that a user's movements are within a tolerance range for movement; and in response to determining that the user's movements are within the tolerance range for movement, transmitting to a client device, via the transceiver, instructions for displaying a message that comprises at least one of text and graphics describing instructions associated with a meditation exercise, the meditation exercise being associated with a target physiological metric (e.g., a target respiration metric). The method may further involve: measuring, based on output of at least one of the one or more biometric sensors, a physiological metric of the user (e.g., a respiration metric of the user's breathing pattern) during the meditation exercise; and determining a performance score indicating the user's performance during the meditation exercise based on comparing the measured physiological metric with the target physiological metric. The method may further involve transmitting to the client device, via the transceiver, based on the performance score, instructions for displaying a message that comprises at least one of text and graphics describing at least one of (i) the performance score and (ii) instructions to the user to adjust the user's performance (e.g., instructions to adjust the user's breathing pattern).

In another aspect, there is provided a wearable device that includes one or more biometric sensors including a motion sensor, as well as a user interface. The wearable device may further include at least one processor and a memory storing computer-executable instructions for controlling the at least one processor to: determine, based on output of the motion sensor, that a user's movements are within a tolerance range for movement; and prompt the user, via the user interface, to perform a meditation exercise in response to determining that the user's movements are within the tolerance range, for movement, the meditation exercise being associated with a target physiological metric. The memory may further store computer-executable instructions for controlling the at least one processor to: measure, based on output of at least one of the one or more biometric sensors, a physiological metric of the user during the meditation exercise; and determine a performance score indicating the user's performance during the meditation exercise based on comparing the measured physiological metric with the target physiological metric. The memory may further store computer-executable instructions for controlling the at least one processor to provide, via the user interface, based on the performance score, feedback information indicative of the performance during the meditation exercise.

In yet another aspect, there is provided a wearable device that includes one or more biometric sensors including a motion sensor, as well as a wireless communication transceiver. The wearable device may further include at least one processor and a memory storing computer-executable instructions for controlling the at least one processor to: determine, based on output of the motion sensor, that a user's movements are within a tolerance range for movement; and in response to determining that the user's movements are within the tolerance range for movement, transmit to a client device, via the transceiver, instructions for displaying a message that comprises at least one of text and graphics describing instructions associated with a meditation exercise, the meditation exercise being associated with a target physiological metric. The memory may further store computer-executable instructions for controlling the at least one processor to: measure, based on output of at least one of the one or more biometric sensors, a physiological metric of the user during the meditation exercise; and determine a performance score indicating the user's performance during the meditation exercise based on comparing the measured physiological metric with the target physiological metric. The memory may further store computer-executable instructions for controlling the at least one processor to transmit to the client device, via the transceiver, based on the performance score, instructions for displaying a message that comprises at least one of text and graphics describing at least one of (i) the performance score and (ii) instructions to the user to adjust the user's performance (e.g., instructions to adjust the user's breathing pattern).

BRIEF DESCRIPTION OF THE DRAWINGS

FIG. 1A is a block diagram illustrating certain components of an example wearable device in accordance with aspects of this disclosure.

DETAILED DESCRIPTION

Figure 1B:
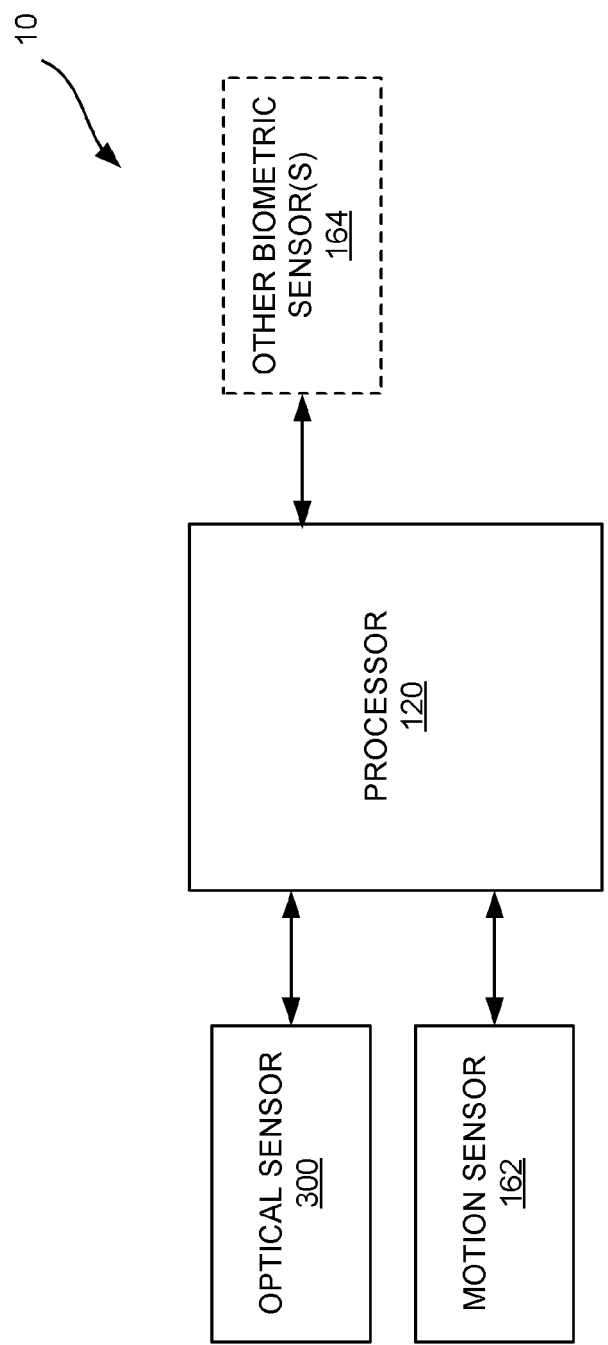
FIG. 1B is a block diagram illustrating example biometric sensors which may be in communication with a processor of a wearable device in accordance with aspects of this disclosure.

An individual may be able to adjust or control his/her physiological state (e.g., their level of calmness or relaxation) by controlling certain voluntary or semi-voluntary processes. For example, when an individual regulates his/her breathing patterns via, for example, slowing his/her breathing rate or breathing more deeply, the individual may induce a calm or relaxed physiological state. A visual display may aid an individual in such breathing regulation via displaying visual instructions to the individual to breathe at a defined rate, to match a defined breathing pattern, and/or to increase the depth of their breathing during inhalation or exhalation, and via displaying feedback information to the individual.

This disclosure relates to methods and devices which may aid and motivate an individual to control their physiological state. An individual may be able to achieve a higher level of control over certain voluntary or semi-voluntary processes when receiving real-time feedback of the process he/she is attempting to control. For example, an individual may be more successful in controlling his/her heart rate when viewing a real-time graph of their heart rate. Such real-time feedback may assist the individual to more effectively induce a calm or relaxed state than solely displaying instructions to the individual.

Wearable Device Overview

FIG. 1A is a block diagram illustrating an example wearable device in accordance with aspects of this disclosure. The wearable device 10 may include a processor 120, a memory 130, a wireless transceiver 140, and one or more biometric sensor(s) 160. The wearable device 10 may also optionally include a user interface 110, and one or more environmental sensor(s) 150. The wireless transceiver 140 may be configured to wirelessly communicate with a client device 20 and/or a server 22, for example, either directly or when in range of a wireless access point (not illustrated). Each of the memory 130, the wireless transceiver 140, the one or more biometric sensor(s) 160, the user interface 110, and/or the one or more environmental sensor(s) 150 may be in electrical communication with the processor 120.

The client device 20 (e.g., a mobile phone, personal computer, tablet computer device, etc.) may be in wireless communication with the processor 120 of the wearable device 10 via the wireless transceiver 140 and may be configured to display instructions and/or feedback to a user of the wearable device 10. For example, in embodiments where the user interface 110 does not include a display component, the wearable device 10 may instead display instructions and/or feedback to the user via a display of the client device 20 that is paired with the wearable device 10. In certain implementations, the wearable device 10 may also communicate with the server 22 via the client device 20 or with the client device 20 via the server 22. The client device 20 and/or the server 22 may receive biometric data from the wearable device 10 in the form of a data steam and may calculate certain metric based on the received data.

The memory 130 may store instructions for causing the processor 120 to perform certain actions. For example, the processor 120 may be configured to provide instructions to a user to perform a meditation or relaxation exercise (e.g., a breathing exercise) and to provide feedback including a performance score indicative of the user's performance during the meditation exercise based on instructions stored in the memory 130. The processor may receive input from the one or more of the biometric sensor(s) 160 and/or the one or more environmental sensors 150 in order to determine the performance score during the exercise. In some embodiments, the biometric sensors 160 may include one or more of an optical sensor (e.g., a photoplethysmographic (PPG) sensor), an accelerometer, and/or other biometric sensor(s). Further information regarding such biometric sensors are described in more detail below (e.g., in connection with FIG. 1B).

The wearable device 10 may collect one or more types of physiological and/or environmental data from the one or more biometric sensor(s) 160, the one or more environmental sensor(s) 150, and/or external devices and communicate or relay such information to other devices (e.g., the client device 20 and/or the server 22), thus permitting the collected data to be viewed, for example, using a web browser or network-based application. For example, while being worn by the user, the wearable device 10 may perform biometric monitoring via calculating and storing the user's step count using the one or more biometric sensor(s) 160. The wearable device 10 may transmit data representative of the user's step count to an account on a web service (e.g., www.fitbit.com), computer, mobile phone, and/or health station where the data may be stored, processed, and/or visualized by the user. The wearable device 10 may measure or calculate other physiological metric(s) in addition to, or in place of, the user's step count. Such physiological metric(s) may include, but are not limited to: energy expenditure (e.g., calorie burn;

floors climbed and/or descended); heart rate; heartbeat waveform; heart rate variability; heart rate recovery; location and/or heading (e.g., via through a global positioning system (GPS), global navigation satellite system (GLONASS), or a similar system; elevation); ambulatory speed and/or distance traveled; step count; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 10 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 10 (and/or the client device 20 and/or the server 22) may collect data from the biometric sensor(s) 160 and/or the environmental sensor(s) 150, and may calculate metrics derived from such data. For example, the wearable device 10 (and/or the client 20 and/or the server 22) may calculate the user's stress or relaxation levels based on a combination of heart rate variability, skin conduction, noise pollution, and/or sleep quality. Any combination of these or other biometrics may be used by the wearable device 10 in determining the performance score indicative of the user's performance during the meditation exercise. These examples are provided for illustration only and are not intended to be limiting or exhaustive.

FIG. 1B is a block diagram illustrating a number of example biometric sensors that may be in communication with the processor of the wearable device in accordance with aspects of this disclosure. For example, in the embodiment of FIG. 1B, the wearable device 10 includes an optical sensor 300 such as, for example, a PPG sensor, which may be used for the detection of a user's heart rate and/or heart rate variability. For example, the wearable device 10 may include the optical sensor 300, a motion sensor 162, and/or other biometric sensor(s) 164. Examples of biometric sensors which may be used as the motion sensor 162 include an accelerometer, a gyroscope, an altimeter, etc. Each of the biometric sensors illustrated in FIG. 1B is in electrical communication with the processor 120 to allow the processor 120 to determine one or more performance score(s) indicative of the user's performance during a meditation exercise. The processor 120 may use input received from any combination of the optical sensor 300, the motion sensor 162, and/or the other biometric sensors 164 to calculate such performance score(s). Further, the biometric data received from the motion sensor 162 and/or other biometric sensors 164 may also be used by the processor 120 to calculate the user's heart rate and/or heart rate variability, as explained in the example below. In some embodiments, the optical sensor 300, the accelerometer 162, and/or the other biometric sensor(s) 164 may correspond to the biometric sensor(s) 160 illustrated in FIG. 1A.

The processor 120 and/or other component(s) of the wearable device 10, according to embodiments and implementations described herein, may be configured to prompt a user to perform a meditation exercise. This prompt may be communicated to the user via a display of the user interface 110 or an external display of a client device 20. In one example, the display of the user interface 110 or the external display of a client device 20 may include a light-emitting circuit. In other implementations, the user prompt may be communicated to the user by producing an audible prompt to the user via a sound-producing circuit or producing a haptic communication to the user via a haptic drive circuit.

Meditation exercises may not be beneficial or effective in altering the user's physiological state (e.g., calming or relaxing the user) unless the user remains still, which may mean, for example, that the user's movements are within a tolerance range for movement. Accordingly, the processor 120 may determine whether the user is still by determining a metric indicative of the user's movement based on an output from the motion sensor 162. For example, the processor 120 may determine that the output of the motion sensor 162 is within a tolerance range for movement prior to initiating the meditation exercise. Further, in some implementations, the processor 120 may (e.g., at intervals) determine whether the user is in a still state by determining whether the output of the motion sensor 162 is within a tolerance range for movement during the meditation exercise. In another example, the user may attempt to start the meditation exercise when the user's motion as measured by the motion sensor 162 it not within the tolerance range for movement. The processor 120 may prompt or notify the user that he/she should perform the meditation exercise at a later time in response to determining that the output of the motion sensor 162 is not within the tolerance range for movement.

During the meditation exercise, the wearable device 10 may prompt the user to breathe according to a target breathing pattern. The wearable device 10 may determine that the user is breathing in accordance with the target breathing pattern by comparing a biometric or physiological measurement (e.g., a respiration metric) of the user's breathing pattern taken during the meditation exercise to a target respiration metric. The processor 120 may determine the respiration metric based on the biometric measurements. In one implementation, the processor 120 may determine a physiological metric based on a heart rate or heart rate variability determined based on measurements of the optical sensor 300.

Figure 2:
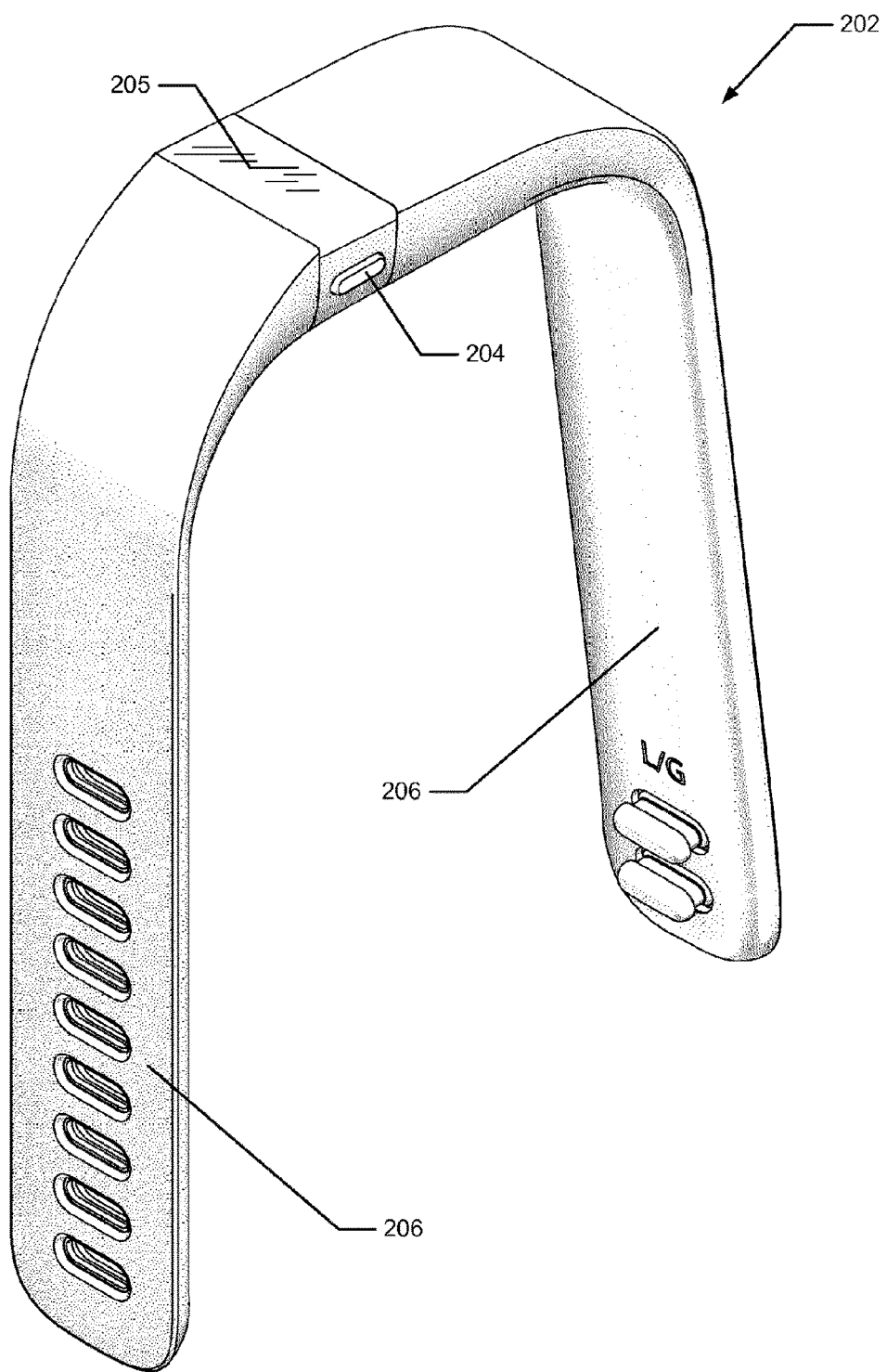
FIG. 2 is an example of a wrist-worn device in accordance with aspects of this disclosure.

The wearable device 10 according to embodiments and implementations described herein may have a shape and/or size adapted for coupling to (e.g., secured to, worn, borne by, etc.) the body or clothing of a user. FIG. 2 shows an example of a wrist-worn wearable device 202 in accordance with aspects of this disclosure. The wrist-worn wearable device 202 may have a display 205, button(s) 204, electronics package (not illustrated), and/or an attachment band 206. The attachment band 206 may be secured to the user through the use of hooks and loops (e.g., Velcro), a clasp, and/or a band having memory of its shape, for example, through the use of a spring metal band.

Figure 3:
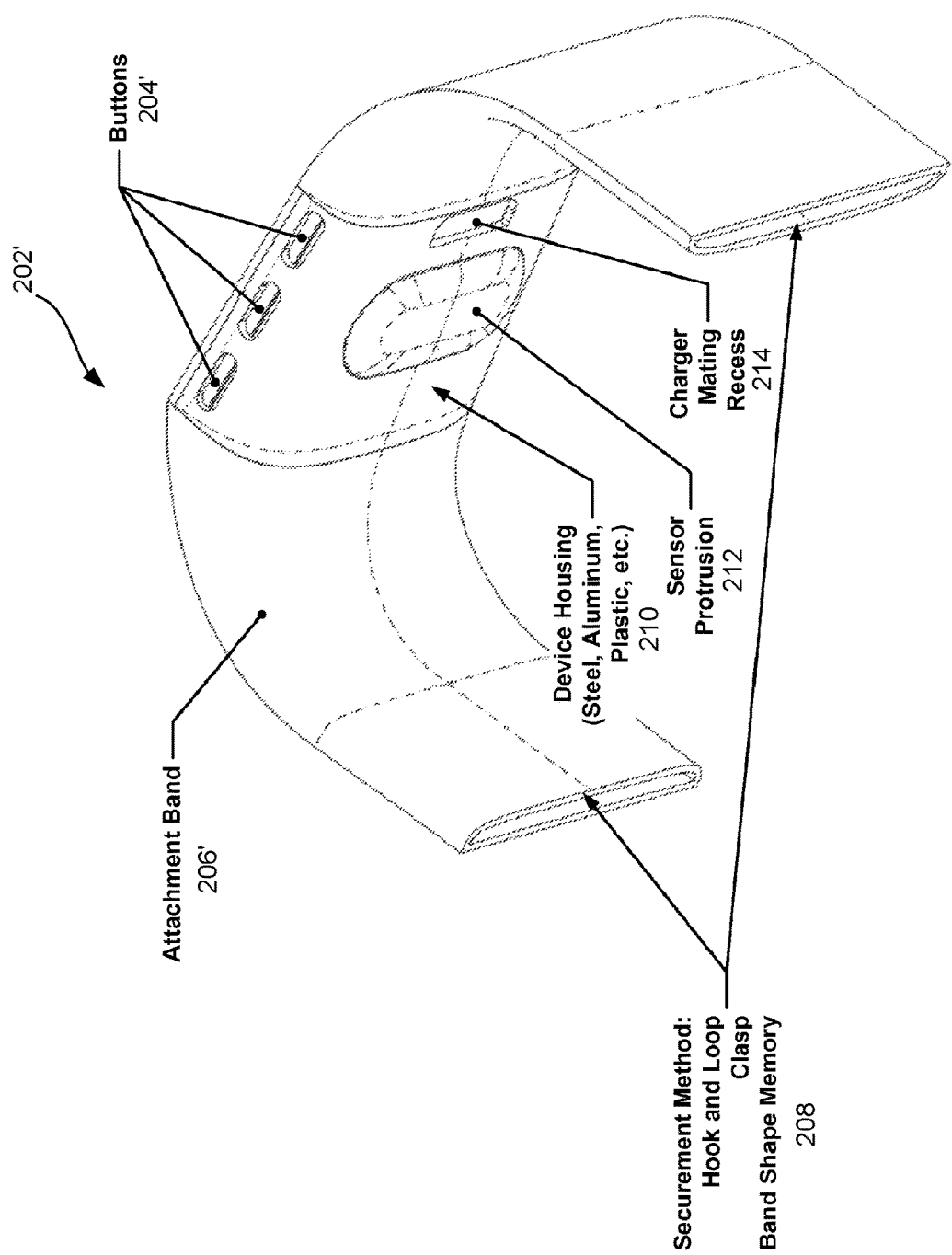
FIG. 3 is a perspective view illustrating another example of a wrist-worn device in accordance with aspects of this disclosure.

FIG. 3 is a perspective view illustrating another example of a wrist-worn device in accordance with aspects of this disclosure. The wrist-worn wearable device 202' of FIG. 3 may include button(s) 204', an attachment band 206', fasteners 208 (e.g., hook and loops, clasps, or band shape memory), a device housing 210, a sensor protrusion 212, and/or a charging/mating recess 214 (e.g., for mating with a charger or data transfer interface of a cable, etc.). In contrast to the wrist-worn wearable device 202 of FIG. 2, in FIG. 3, the wrist-worn wearable device 202' includes the sensor protrusion 212 and the recess 214 for mating with a charger and/or data transmission cable. FIG. 3 also illustrates the device housing 210 which may house internals of the wrist-worn wearable device 202' such as, for example, the processor 120, the optical sensor 300, and/or the motion sensor 162 (shown in FIG. 2). The optical sensor 300 may be housed directly below the sensor protrusion 212. The optical sensor 300 is described in further detail below in connection with FIGS. 4 to 5B.

Optical Sensor

In accordance with one or more aspects of the present disclosure, in order to provide biofeedback during a meditation exercise, the wearable device 10 may use one or more of the biometric sensor(s) 160 to determine a physiological metric of the user (e.g., a respiration metric based on the user's breathing pattern) during the exercise. For example, an optical sensor 300 may be used to detect and measure features of a cardiac signal of the user. In certain embodiments, the optical sensor 300 may be a PPG sensor. The term "optical sensor" may be used interchangeably with a PPG sensor 300 hereinafter; however, in certain embodiments, the optical sensor may comprise a non-PPG sensor.

Figure 4:
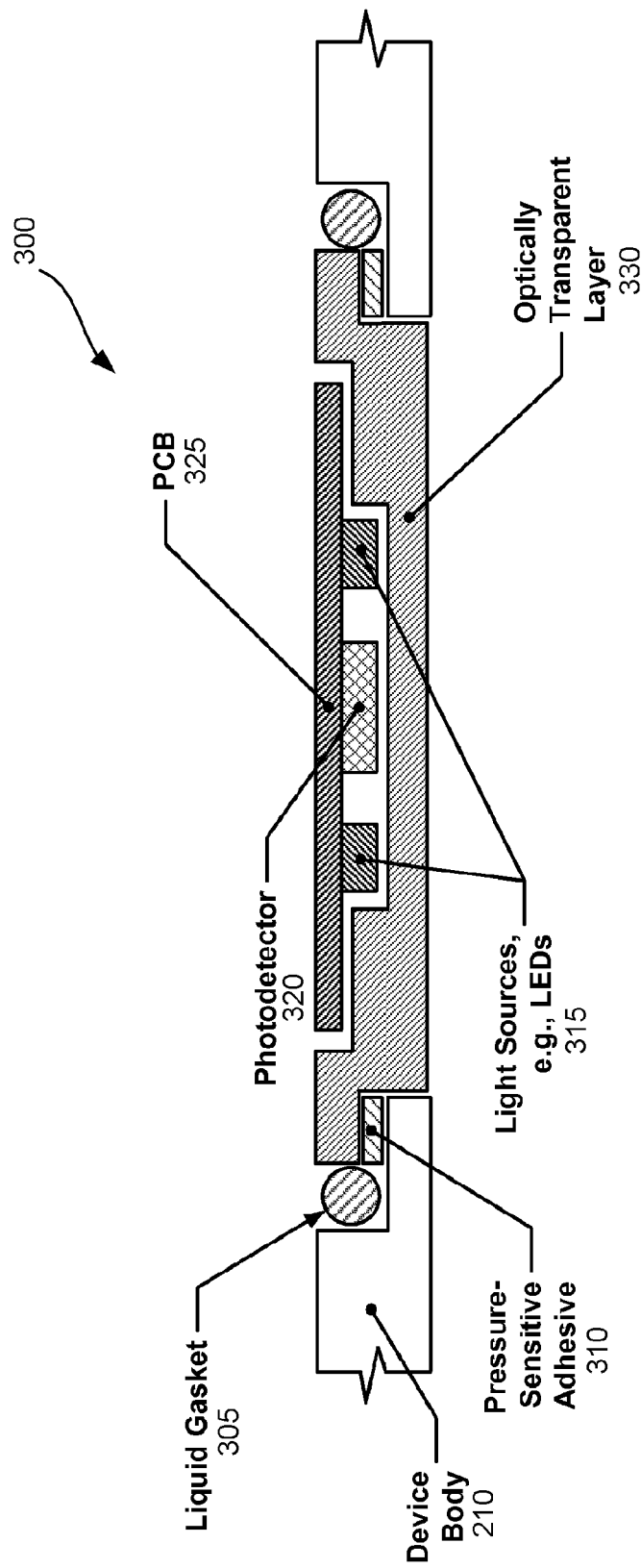
FIG. 4 is a cross-sectional view of an example wearable device that includes an optical sensor in accordance with aspects of this disclosure.

FIG. 4 is a cross-sectional view of a portion of a wearable device that includes an optical sensor in accordance with aspects of this disclosure. In the embodiment of FIG. 4, the optical sensor 300 may be implemented as a PPG sensor 300. The PPG sensor 300 may be formed within the device body 210 and may include one or more light sources (e.g., light-emitting diodes (LEDs)) 315, a photodetector 320, a printed circuit board (PCB) 325, and an optically transparent layer 330. The optically transparent layer 330 may be attached to the device body 210 via a pressure-sensitive adhesive 310 and a liquid gasket 305 may be provided to seal the wearable device 10.

In the embodiment of FIG. 4, the two light sources 315 may be placed on either side of the photodetector 320 to facilitate PPG sensing. The number of light sources 315 may vary in other implementations. Depending on the embodiment, the light sources 315 may emit green light, infrared light, or light having multiple wavelengths, (e.g., red, green, and infrared light or any combination thereof). In certain embodiments, a light-blocking material (not illustrated) may be placed between the light sources 315 and the photodetector 320 to prevent any light from the light sources 315 from reaching the photodetector 320 without first exiting the body of the wearable device 10. An optically transparent layer 330 may be placed on the lower surface of the PPG sensor 300 to form a seal. Although the optically transparent layer 330 is illustrated as being flush with the device body 210, in other embodiments, the optically transparent layer 330 may form a protrusion as shown in FIG. 3. The optically transparent layer 330 may serve other functions such as preventing liquid or debris from entering the wearable device 10 where the light source(s) 315 or the photodetector(s) 320 are placed. The optically transparent layer 330 may be formed through in-mold labeling (IML). The light source(s) 315 and the photodetector(s) 320 may be placed on the PCB 325, which may be flexible in certain embodiments.

The configuration of FIG. 4 may improve the efficiency of light flux coupling between the components of the optical sensor 300 and the user's body. For example, in one embodiment, the light source(s) 315 and/or the associated detector(s) 320 may be disposed on a flexible or pliable substrate, such as PCB 325, that may flex, allowing the skin-side of the wearable device 10, which may be made from a compliant material, to conform (e.g., without additional processing) or be capable of being shaped (or compliant) to conform to the shape of the body part (e.g., the user's wrist, arm, ankle, and/or leg) to which the wearable device 10 is coupled to or attached during normal operation so that the light source(s) 315 and/or the associated detector(s) 320 is/are close to the skin of the user (i.e., with little to no gap between the skin-side of the device and the adjacent surface of the skin of the user).

In one embodiment, the light source(s) 315 and/or the associated detector(s) 320 may be disposed on a Flat Flex Cable (FFC) or flexible PCB 325. In one aspect, the flexible or pliable substrate (e.g., an FFC or flexible PCB 325) may connect to a second substrate (e.g., PCB) within the device having other components disposed thereon (e.g., the data processing circuitry). Optical components of differing heights may be mounted to different portions or protrusions of a flexible substrate and pressed or secured to the housing surface such that the optical components are flush to the housing surface. In another aspect, the second substrate may be a relatively inflexible or non-pliable substrate, fixed within the device, having other circuitry and/or component(s) (passive and/or active) disposed thereon.

In related aspects, the PPG circuitry may include amplification circuitry optimized to obtain quality signals regardless of environmental conditions including, but not limited to, motion, ambient light, and skin color. Two examples of such PPG amplification circuitry are described in connection with FIGS. 5A and 5B.

Figure 5A:
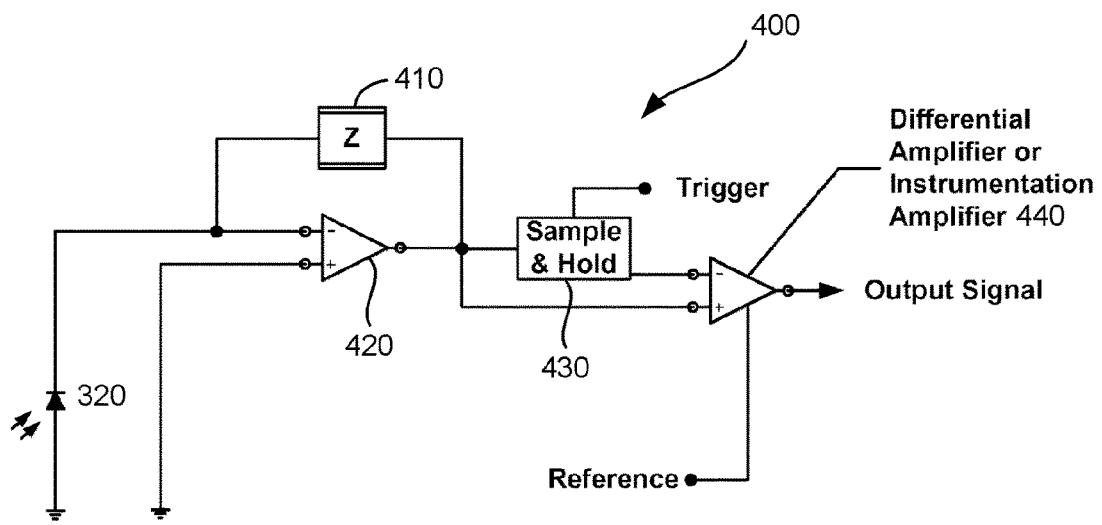
FIGS. 5A and 5B are example schematics of circuits used for a photoplethysmographic (PPG) sensor in accordance with aspects of this disclosure.

FIG. 5A illustrates an example schematic of a sample-and-hold circuit and differential/instrumentation amplifier which may be used in PPG sensing. The example circuitry 400 of FIG. 5A may include a photodetector 320, a feedback reactance 410, an amplifier 420 (e.g., a differential amplifier), a sample-and-hold circuit 430 (e.g., a buffer), and a differential or instrumental amplifier 440. The output of the photodetector 320 may be connected to a first input of the amplifier 420 (e.g., the negative terminal) to be compared with a ground signal (or another signal) connected to a second input of the amplifier 420 (e.g., the positive terminal). The output of the amplifier 420 may be connected to the same input (e.g., the first input) of the amplifier as the photodetector 320. The output of the amplifier 420 may also be connected to the sample-and-hold circuit 430 and a first input of the differential/instrumentation amplifier 440 (e.g., the positive terminal). The output of the sample-and-hold circuit 430 may also be connected to a second input of the differential/instrumental amplifier 440 (e.g., the negative terminal). The differential/instrumental amplifier 440 may then output a comparison between the amplified photodetector 320 output and a previously sampled amplified photodetector 320 output. The output signal from the circuit 400 may therefore be an amplified difference between a current sample and a previous sample of the photodetector 320, referenced to a given voltage.

Figure 5B:
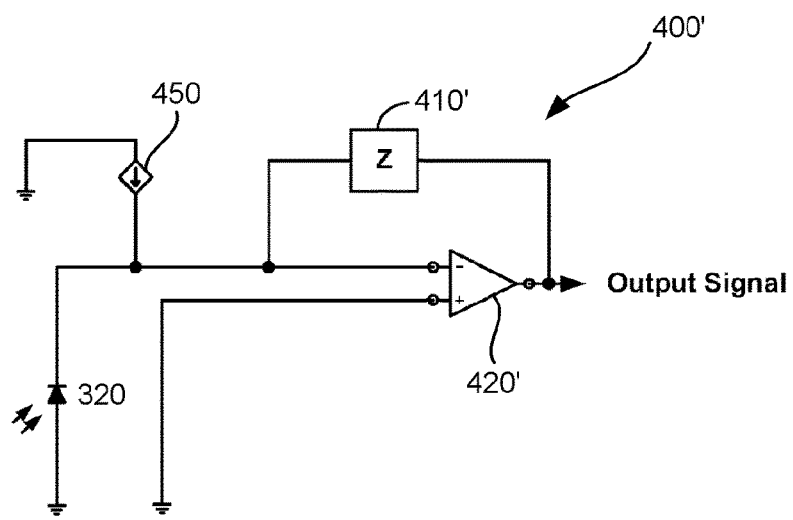

FIG. 5B illustrates an example schematic of a circuit for a PPG sensor using a controlled current source to offset "bias" current prior to a transimpedance amplifier. The circuit 400' of FIG. 5B may include a photodetector 320, a current source 450, a feedback impedance 410', and an amplifier 420' (e.g., a differential amplifier). The output of the photodetector 320 may be combined with the output of the current source 450 and then supplied to a first input of the amplifier 420' (e.g., the negative terminal). A second input of the amplifier 420' (e.g., the positive terminal) may be connected to ground or another potential. The output signal from the amplifier 420' may be fed back to the first input of the amplifier 420' connected to the photodetector 320 via the loop with the feedback impedance 410'. This arrangement of circuit components may allow for a greater gain to be applied at the transimpedance amplifier stage.

In accordance with one or more aspects of the present disclosure, as described above, the processor 120 may be configured to determine the heart rate or heart rate variability of the user based on the output of the PPG sensor 300 in accordance with aspects of this disclosure. In some embodiments, the wearable device 10 may include further components that can be implemented in hardware or via the processor 120 to incorporate measurements from other biometric sensors 160 in the determination of one or more physiological metrics (e.g., respiration metrics, the heart rate of the user, etc.). In one example, the motion sensor 162 may be used to augment the output of the PPG sensor in determining the heart rate of the user.

Measuring Heart Rate and/or Heart Rate Variability

Figure 6A:
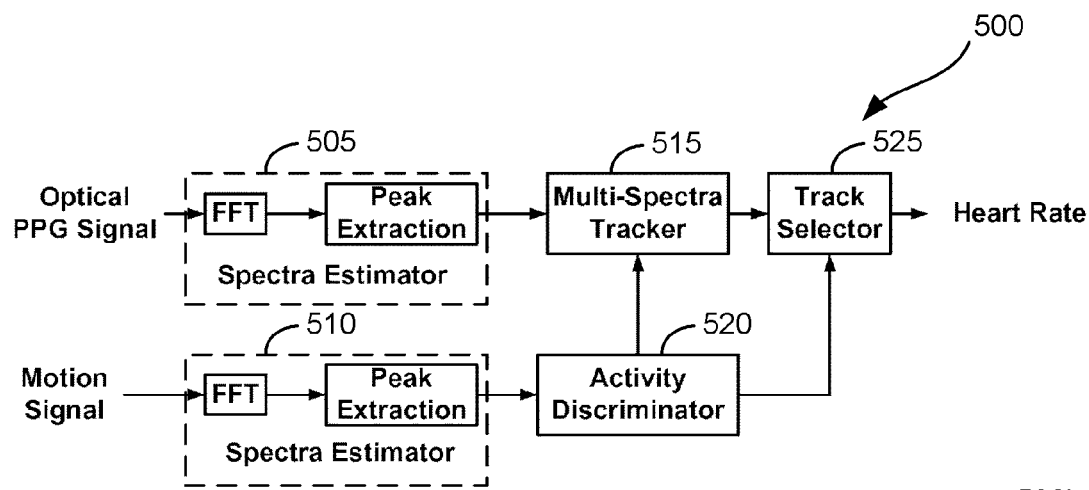
FIGS. 6A and 6B are example block diagrams used for determining heart rate in accordance with aspects of this disclosure.
Figure 6B:
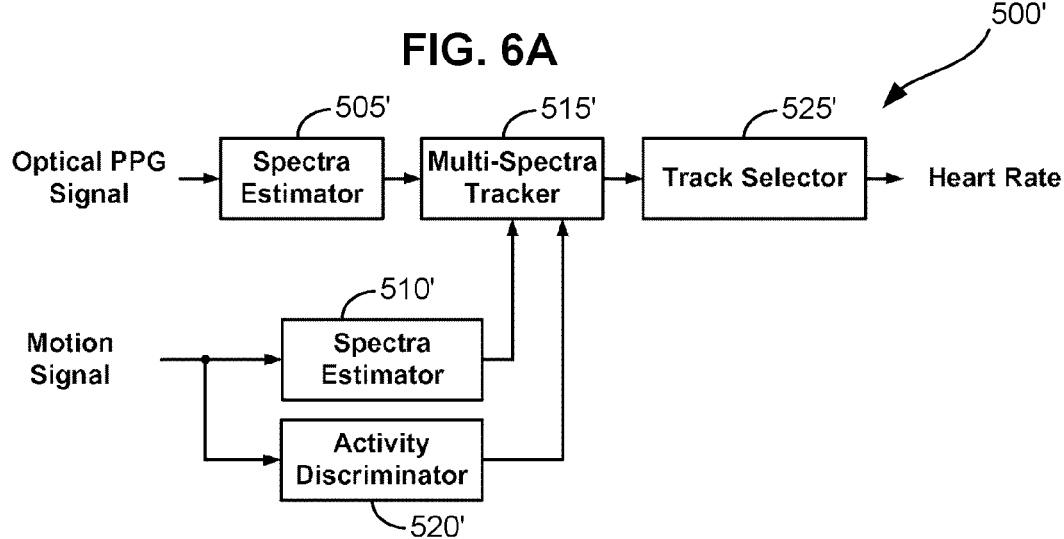

FIGS. 6A and 6B are example block diagrams used for determining heart rate in accordance with aspects of this disclosure. As shown in FIG. 6A, the wearable device 10 may include a system 500 of components for determining the heart rate of the user based on an optical PPG signal (e.g., received from the PPG sensor 300) and a motion signal (e.g., received from the motion sensor 162). The system 500 may be implemented by hardware components and/or in software executed by the processor 120. The system 500 may include first and second spectra estimators 505 and 510, a multi-spectra tracker 515, an activity discriminator 520, and a track selector 525. Each of the first and second spectra estimators 505 and 510 may include a Fast Fourier Transform (FFT) block and a peak extraction block. In the example of FIG. 6A, the activity discriminator 520 may use the peaks extracted from the motion signal in a determination of the activity that the user is performing (e.g., sedentary, walking, running, sleeping, lying down, sitting, biking, typing, elliptical, weight training). This determination of the current activity of the user may be used by the multi-spectra tracker 515 and the track selector 525 in extracting the heart rate from the optical PPG signal. Thus, the motion signal in FIG. 6A may be used by the system 500 to determine the current activity of the user.

The blocks illustrated in FIGS. 6A and 6B are merely examples of components and/or processing modules that may be performed to supplement a PPG signal with a motion signal to determine heart rate. However, in other implementations, the system 500 may include other blocks or may include input from other biometric sensors of the wearable device 10.

In the implementation of FIG. 6B, the system 500' includes first and second spectra estimators 505' and 510', a multi-spectra tracker 515', an activity discriminator 520', and a track selector 525'. Each of the first and second spectra estimators 505 and 510 may include a Fast Fourier Transform (FFT) block and a peak extraction block. In the example of FIG. 6B, the peaks extracted from the motion signal by the spectra estimator 510' may be supplied to the multi-spectra tracker 515'. Accordingly, the peaks from the motion signal may be used by the multi-spectra tracker 515' in addition to the peaks in the optical PPG signal and the current activity determined by the activity discriminator 520' in the determination of the heart rate.

Under certain operating conditions, the heart rate of the user may be measured by counting the number of signal peaks within a time window or by utilizing the fundamental frequency or second harmonic of the signal (e.g., through an FFT). In other cases, such as heart rate data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signal and the output may be used to do activity discrimination (e.g., sedentary, walking, running, sleeping, lying down, sitting, biking, typing, elliptical, weight training) which may be used to assist the multiple-target tracker 515 or 515'. For instance, it may be determined that the user was stationary and has begun to move. This information may be used to by the multi-spectra tracker 515 or 515' to bias the track continuation toward increasing frequencies. Similarly, the activity discriminator 520 or 520' may determine that the user has stopped running or is running slower and this information may be used to preferentially bias the track continuation toward decreasing frequencies.

Tracking may be performed by the multi-spectra tracker 515 or 515' with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 525 or 525' may use the output tracks from the multiple-spectra tracker 515 or 515' and estimate the user's heart rate based on the output tracks. The track selector 525 or 525' may estimate a probability for each of the tracks that the corresponding track is representative of the user's heart rate. The estimate may be taken as the track having the maximum probability of being representative of the user's heart rate, a sum of the tracks respectively weighted by their probabilities of being representative of the user's the heart rate, etc. The activity discriminator 520 or 520' may determine a current activity being performed by the user which may be used by the track selector 525 or 525' in estimating the user's heart rate. For instance, when the user is sleeping, sitting, lying down, or sedentary, the user's estimated heart rate may be skewed toward heart rates in the 40-80 bpm range. When the user is running, jogging, or doing other vigorous exercise, the user's estimated heart rate may be skewed toward elevated heart rates in the 90-180 bpm range. The activity discriminator 520 or 520' may determine the user's current activity based at least in part on the speed of the user. The user's estimated heart rate may be shifted toward (or wholly obtained by) the fundamental frequency of the selected output track when the user is not moving. The output track that corresponds to the user's heart rate may be selected by the track selector 525 or 525' based on criteria that are indicative of changes in activity. For instance, when the user begins to walk from being stationary, the track selector 525 or 525' may select the output track that illustrates a shift toward higher frequency based on output received from the activity discriminator 520 or 520'.

Figure 7A:
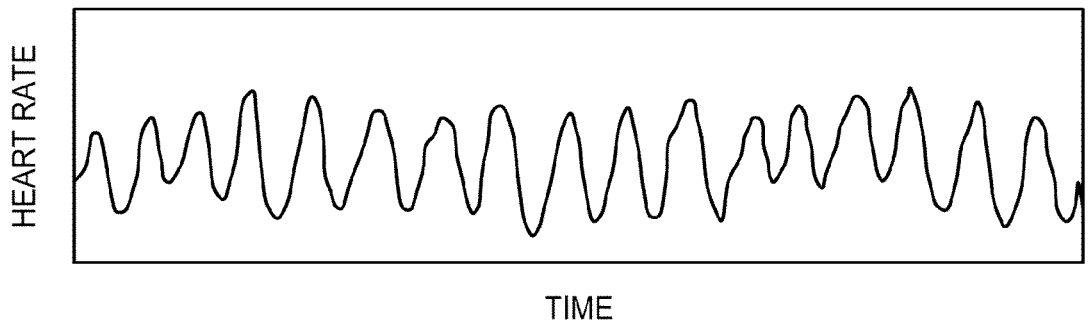
FIGS. 7A and 7B are graphs illustrating examples of the heart rate measured by an optical sensor in accordance with aspects of this disclosure.
Figure 7B:
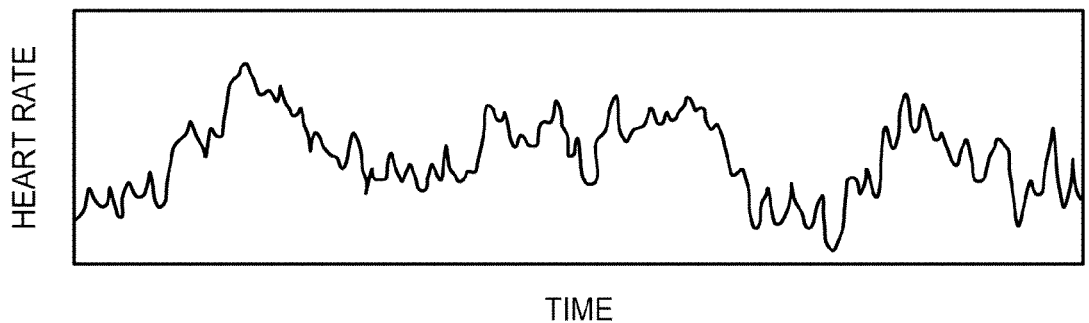

FIGS. 7A and 7B are graphs illustrating examples of the heart rate measured by an optical sensor in accordance with aspects of this disclosure. The heart rate illustrated in FIG. 7A may be indicative of a heart rate measured by the PPG sensor 300 during a meditation exercise. As shown in FIG. 7A, the heart rate of the user may regularly vary in a sinusoidal fashion. The variation in the heart rate measurements may be referred to as heart rate variability. For certain individuals, higher heart rate variabilities may be indicative of the individual being in a more calm or relaxed physiological state than for lower heart rate variabilities. As such, in certain implementations, the heart rate variability may be used as a physiological metric used in the determination of a performance score that indicates the physiological state of the user. The heart rate variability illustrated in FIG. 7A may indicate that the user is in a relaxed or calm state. However, other physiological metrics may also be used in the determination of the performance score indicating the user's performance during the meditation exercise, as will be described in further detail below.

The heart rate illustrated in FIG. 7B may be indicative of a heart rate measured by the PPG sensor 300 while the user is in an excited or stressed physiological state. As shown in FIG. 7B, the variations in the user's heart rate are less regular than the heart rate illustrated in FIG. 7A. As such, the heart rate illustrated in FIG. 7B may be indicative that the user is not following the meditation exercise properly and/or is not benefiting from the meditation exercise. In certain implementations, the processor 120 of the wearable device 10 may determine a performance score indicating the user's performance during the meditation exercise based on the characteristics of the user's heart rate variability. For example, if the user has a heart rate measurement as shown in FIG. 7B at the beginning of the exercise, and thus has a low heart rate variability, but the user's heart rate variability increases to a level closer to the heart rate variability of FIG. 7A during the meditation exercise, the processor 120 may increase the user's performance score.

The processor 120 may also suggest that the user may benefit from performing the meditation exercise based on physiological metrics (e.g., respiration metrics) determined from the output of the PPG sensor 300. In certain implementations, the processor 120 may determine that the user has a low heart rate variability by analyzing the PPG sensor 300 output, for example, at various intervals during the day. When the PPG sensor 300 output is indicative of the user having a stressed physiological state (e.g., the user has a low heart rate variability), the wearable device 10 may suggest that the user perform the meditation exercise.

However, heart rate variability may not be indicative of stress levels for certain individuals. For example, individuals with a high fitness level may have a high heart rate variability regardless of their calmness or relaxation level. With a high heart rate variability baseline, changes in the user's heart rate variability may not adequately reflect the user's change in physiological state, leading to the processor 120 determining a performance score that may not accurately reflect this change in the user's physiological state. In order to account for such individuals, the processor 120 may determine a baseline heart rate variability based on measurements taken by the PPG sensor 300 at times other than the meditation exercise. The processor 120 may determine the baseline based on the PPG measurements, for example, when the output of the motion sensor 162 is within a tolerance range for movement. When the user's baseline heart rate variability is relatively high (e.g., higher than an average heart rate variability for other individuals), the processor 120 may calibrate the determination of the performance score to be more sensitive (e.g., compared to the other individuals) to changes in the user's heart rate variability. The processor 120 may determine to perform the calibration based on a comparison of the user's baseline heart rate variability to a defined threshold.

In one example, the processor 120 may be configured to determine the performance score indicating the user's performance during the exercise based on the heart rate or heart rate variability detected by the optical sensor 300. For example, the processor 120 may determine a heart rate or heart rate variability similar to the heart rate and heart rate variability illustrated in FIGS. 7A and 7B based on the output of the optical sensor 300. As described below, the processor 120 may estimate certain respiration metrics of the user's breathing pattern based on the measured heart rate or heart rate variability. The estimated respiration metrics may include, for example, at least one of: (i) the user's breathing rate; (ii) the timing, depth, and/or duration of the user's inhalation; (iii) the timing, depth, and/or duration of the user's exhalation; and/or (iv) the consistency and/or variability of one or more of (i), (ii), and (iii). The processor 120 may calculate the performance indicator based on one or more of the estimated respiration metrics of the user's breathing pattern.

In other implementations, the processor 120 of the wearable device 10 may determine the performance score based on other respiration metrics determined from the measured heart rate or from other biometric data. These other respiration metrics may provide a more accurate performance score for certain individuals, such as individuals with a high fitness level. In certain implementations, the processor 120 may determine a respiration metric based on the heart rate or heart rate variability measured by the PPG sensor 300. The respiration metric may be indicative of a number of aspects of the user's breathing pattern. For example, as noted above, the respiration metric may include, but is not limited to, the timing, depth, and/or duration of the user's inhalation/exhalation. In certain circumstances, the heart rate of an individual may increase during inhalation and may decrease during exhalation. Additionally, the depth of the user's breathing may affect the user's heart rate or heart rate variability since during a deep breath the user's lungs expand more, which may change the timing between each pulse of the user's heart pattern. Thus, by monitoring the user's heart rate and/or heart rate variability with respect to a target respiration metric while the user is not moving or has at least minimized movement (e.g., when the output of the motion sensor 162 is within a tolerance range for movement), the processor 120 may determine that certain changes in the user's heart rate and/or heart rate variability are due to the user's breathing pattern. The processor 120 may thus determine one or more of the above-indicated respiration metrics based on the measured user's heart rate and/or heart rate variability. As such, the processor 120 may determine a performance score based on how close the respiration metric is to the target respiration metric, which may be part of an overall target breathing pattern.

The target breathing pattern may vary depending on the type of the meditation or breathing exercise. In one example, the target breathing pattern may include a smooth (e.g., sinusoidal) breathing pattern. In another example, the target breathing pattern may include a cycle of the user breathing in, holding his/her breath, and breathing out. In still another example, the target breathing pattern may include different intervals for breathing in and/or breathing out (e.g., the interval for breathing in may be about half of the interval for breathing out). The processor 120 may determine the performance score based at least in part on how closely the measured respiration metric(s) of the user's breathing pattern match the target respiration metric(s) of the target breathing pattern.

The processor 120 may also determine the performance score indicating the user's performance during the meditation exercise based on one or more of a number outputs from different biometric sensors 160. For example, the physiological metric determined by the processor 120 may include at least one of: user heart rate, user PPG, user blood pressure, user respiration rate, user skin conduction, user blood glucose levels, user blood oxygenation, user skin temperature, user body temperature, user electromyography, and/or user electroencephalography (EEG).

Instructions and Feedback Regarding Meditation Exercise

The processor 120 may display feedback to the user during the meditation exercise in order to aid and/or motivate the user to achieve greater control over their breathing pattern and/or other voluntary or semi-voluntary processes. For example, the processor 120 may use the user interface 110 or a display of a client device (e.g., a mobile phone) to display the feedback to the user. The displayed feedback may include the determined performance score, the user's heart rate, and/or the user's heart rate variability. The feedback may be displayed concurrently with or shortly after the instructions to the user to perform the meditation exercise.

Figure 8A:
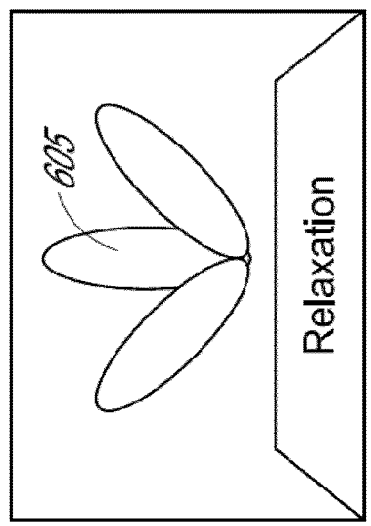
FIGS. 8A-8L are example images or user interfaces that may be displayed to a user in accordance with aspects of this disclosure.

FIGS. 8A-8L are example images or user interfaces (e.g., graphical and/or textual user interfaces) that may be displayed to a user in accordance with aspects of this disclosure. FIGS. 8A-8G illustrate a number of images which may be displayed to the user during the execution of an exemplary application or program on a client device 20 and/or wearable device 10. FIG. 8A may be an image displayed prior to the beginning of the meditation exercise. For example, FIG. 8A may be a splash screen that is displayed while the program for the meditation exercise is loaded from the memory 130. The splash screen may include a logo or image 605 associated with the meditation exercise (and/or an application or program that provides the meditation exercise) to inform the user that the meditation exercise is loading.

Figure 8B:
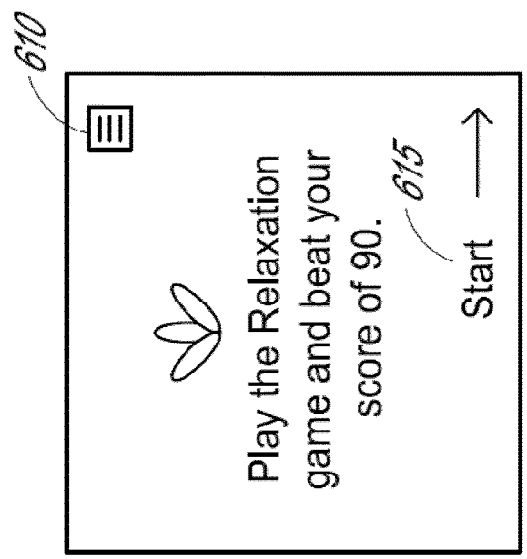

FIG. 8B may be an image including a number of selectable boxes for the user to navigate through the meditation exercise application. The image may include a message generated based on data stored from past meditation exercises performed by the user. For example, the image may prompt the user to attempt to achieve a higher performance score than the previous score attained by the user. The image may also include a menu button 610 to allow the user to open a menu and a start button 615 to allow the user to start the meditation exercise.

Figure 8C:

After the user selects the start button 615, the image of FIG. 8C may be displayed. This image may include a message for the user to be still (e.g., minimize or reduce the user's movements) and prepare for the meditation exercise. The top of the image may include a count-down to the beginning of the meditation exercise. Since the meditation exercise may not be effective if the user is moving, the wearable device 10 may use input from the motion sensor 162 to determine whether the movement of the user is within a tolerance range for movement. When the user's movements are not within the tolerance range, the processor 120 may delay the prompting of the user to perform the meditation exercise, or delay the start of the meditation exercise, or delay the measuring of the physiological metric of the user (e.g., the respiration metric of the user's breathing pattern). When the user's movements are within the tolerance range, the processor 120 may proceed with displaying the meditation instructions once the warm up time has elapsed.

Figure 8D:
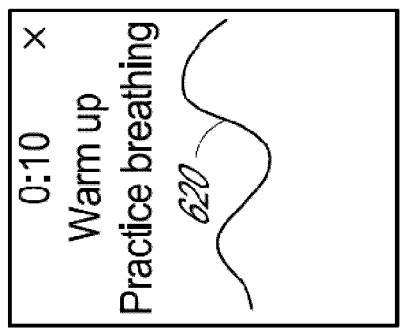
Figure 8E:
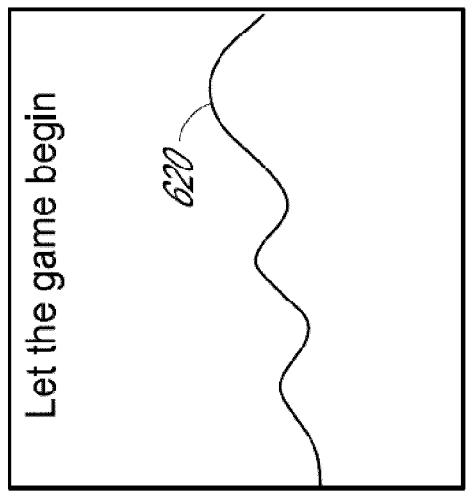

In one example, the image of FIG. 8D may be displayed for a defined period of time prior to the start of the meditation exercise. This image may instruct the user to practice breathing and may include real-time feedback information 620 regarding one of the user's measured biometrics. For example, the feedback may be the heart rate or heart rate variability measured by the PPG sensor 300. Thereafter, the image of FIG. 8E may be displayed indicating that the meditation exercise has begun. In one example, the feedback information 620 may be maintained on the image throughout the meditation exercise.

Figure 8F:
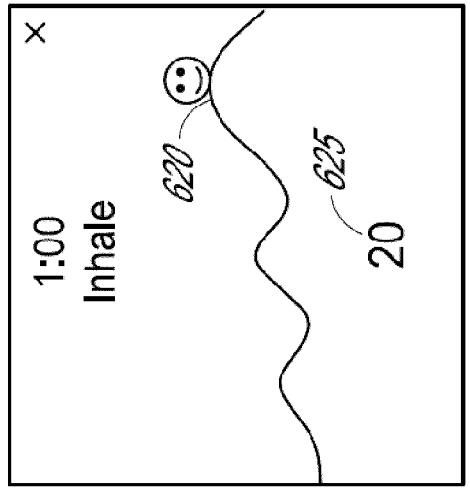
Figure 8I:
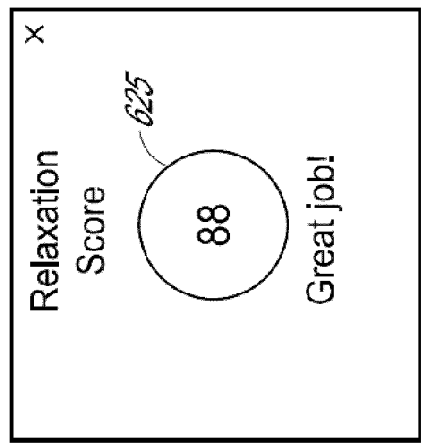
Figure 8H:
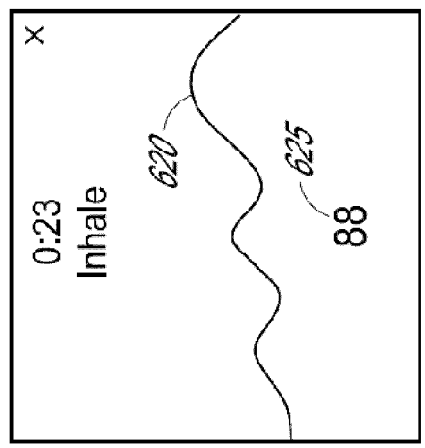
Figure 8G:
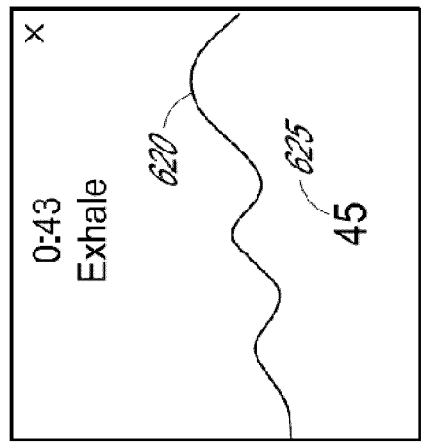

FIGS. 8F-H may then be displayed to the user during the meditation exercise. A timer may be displayed on the top of the images to inform the user as to the remaining time in the exercise. The feedback information 620 may also be displayed throughout the meditation exercise. Additionally, once the meditation exercise has started, the performance indicator 625 may also be displayed to the user. As shown in the image of FIG. 8F, the top of the image may include a prompt to the user to inhale. Thereafter, as shown in the image of FIG. 8G, the prompt to the user may change to prompt the user to exhale. During the meditation exercise, the processor 120 may determine a performance indicator 625 continuously or at defined time intervals. As the measured biometric data changes to reflect changes in the breathing pattern or physiological state of the user, the performance indicator 625 may also change. The meditation exercise may result in changes in the user's biometric measurements such as, for example, the user's heart rate may indicate the extent to which the user's breathing patterns, including the timing and depth thereof, match the target breathing pattern. Thus, the value of the performance indicator 625 may increase when the user's breathing patterns approach the target breathing pattern. The performance indicator 625 of FIG. 8H may indicate that the user's biometric measurements substantially match the target breathing pattern.

Figure 8J:
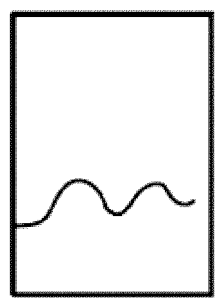
Figure 8J:
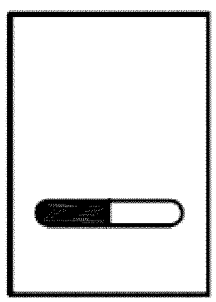
Figure 8J:
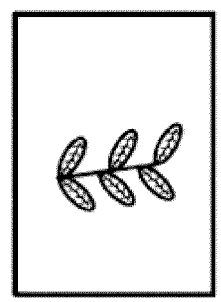
Figure 8J:
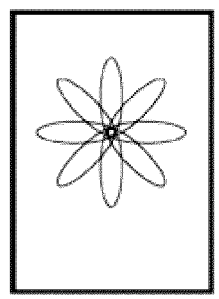
Figure 8J:
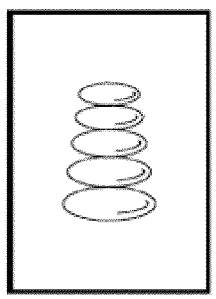
Figure 8J:
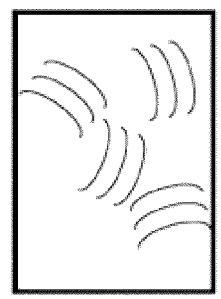
Figure 8K:
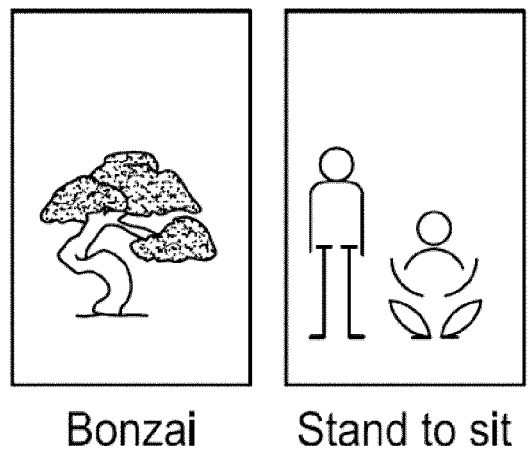
Figure 8L:
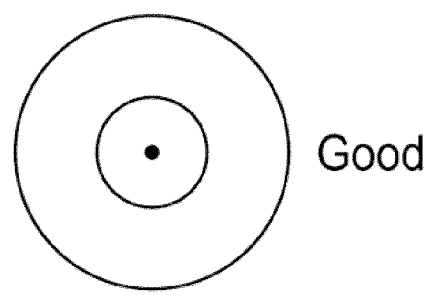

In one example, once the meditation exercise is complete, the image of FIG. 8I may be displayed. In another example, the image of FIG. 8I may be displayed after completion of a segment or portion of the meditation exercise. This image may display the performance indicator along with a message indicating that the meditation exercise (or segment thereof) is over. A number of other images may be displayed as shown in FIG. 8J which may include a visualization of the value of the performance indicator 625 from the meditation exercise or may indicate progression of the performance indicator over a number of meditation exercises. For example, a heart rate line may indicate the user's heart rate as measured during the meditation exercise. A bar, growing flower/lotus, Zen rocks, and/or Zen lines may correspond to and be a visualization of the value of the performance indictor 625 (e.g., the length of the filled in portion of the bar or the length of the growing flower/lotus may be based on the value of the performance indicator 625). Alternatively, any one of the bar, growing flower/lotus, Zen rocks, and/or Zen lines may be animated or change with respect to a previously displayed version to show progress of the performance indicator over a number of past meditation exercises. The images of FIG. 8K may be displayed to show progress of the performance indicator 625 over time. For example, the bonsai tree may grow in relation to a change in the performance indicator or the stand to sit image(s) may show progress of a person from a standing pose to a sitting pose. Similarly, the image of FIG. 8L may be displayed during or after the meditation exercise. This image of FIG. 8L may indicate, for example, that the user has met a target performance goal during the meditation exercise and may be, for example, a "target" or a "bull's eye". In related aspects, the processor 120 may adjust the target performance goal for the next meditation exercise if the user has met the current target performance goal.

In some embodiments, the processor 120 may display meditation exercise instructions that correspond to an object or shape (e.g., a circle) that changes in one manner (e.g., expands, or changes color to a first color) to indicate when the user should breath in and that changes in another manner (e.g., contracts, or changes color to a second color) to indicate when the user should breath out.

In some embodiments, the processor 120 may provide meditation exercise instructions via audio output or haptic output. For example, the wearable device 10 may vibrate, buzz, move, or emit a sound (e.g., a beep or verbal instruction) to indicate when a meditation exercise is starting or ending, or to indicate when the user should start to inhale, start to exhale, etc.

In some embodiments, the processor 120 may prompt the user to input their assessment of their current stress level before the meditation exercise has begun. For example, the processor 120 may display a user interface via the wearable device 10 (e.g., see user interface 110 in FIG. 1A) or another device (e.g., client device 20), where the displayed user interface enables the user to rate their stress level as a value in a range of values (e.g., 1 to 10, 1 to 100, etc.). After the meditation exercise is completed, the processor 120 may again prompt the user to input their assessment of their current stress level after the meditation exercise. Accordingly, the processor 120 may log and determine the effectiveness of one or more meditation exercises for one or more users (e.g., where a first meditation exercise having the greatest difference between the inputted before and after stress values is ranked higher than a second meditation exercise having a smaller difference between the inputted before and after stress values).

In some embodiments, the processor 120 may enable a user to adjust aspects of a meditation exercise. For example, the processor 120 may display a user interface via the wearable device 10 (e.g., see user interface 110 in FIG. 1A) or another device (e.g., client device 20), where the displayed user interface includes user-adjustable settings that enable the user to increase or decrease a duration of meditation exercise, a pace or timing of breathing associated with a breathing exercise, and so on.

Flowcharts of Example Methods for Providing Biofeedback During Meditation Exercise(s)

Figure 9:
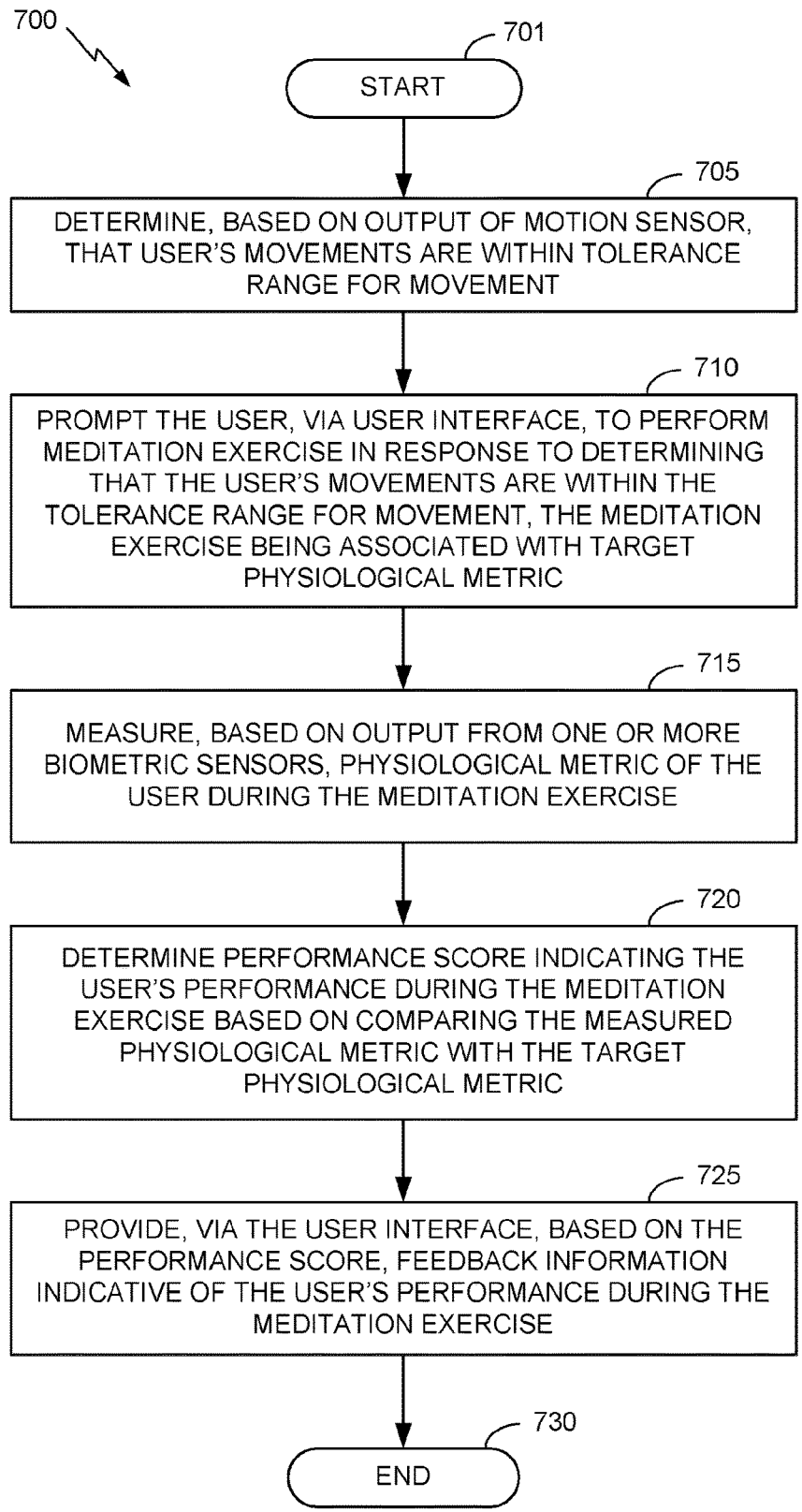
FIG. 9 is a flowchart illustrating an example method for providing biofeedback during a meditation exercise in accordance with aspects of this disclosure.

FIG. 9 is a flowchart illustrating an example method operable by a wearable device 10, or component(s) thereof, for providing biofeedback during a meditation exercise in accordance with aspects of this disclosure. For example, the steps of method 700 illustrated in FIG. 9 may be performed by a processor 120 of a wearable device 10 or an entity in communication with the wearable device 10. For example, the wearable device 10 may be in communication with a client device 20 (e.g., a mobile phone, etc.) which can perform the method 700 or portions thereof. For convenience, the method 700 is described as performed by the processor 120 of the wearable device 10.

In one implementation, the wearable device 10 comprises one or more biometric sensors 160 including a motion sensor 162, a user interface 110, and the processor 120. The method 700 begins at block 701. At block 705, the processor 120 determines, based on output of the motion sensor 162, that a user's movements are within a tolerance range for movement. At block 710, the processor 120 prompts the user, via the user interface 110, to perform a meditation exercise in response to determining that the user's movements are within the tolerance range for movement. The meditation exercise may comprise or be associated with a target physiological metric (e.g., a target respiration metric).

At block 715 the processor 120 measures, based on output of at least one of the one or more biometric sensors 160, a physiological metric of the user (e.g., a respiration metric of the user's breathing pattern) during the meditation exercise. At block 720, the processor 120 determines a performance score indicating the user's performance during the meditation exercise based on comparing the measured physiological metric with the target physiological metric. At block 725, the processor 120 provides, via the user interface 110, based on the performance score, feedback information indicative of the user's performance during the meditation exercise. The method ends at block 730.

Figure 10:
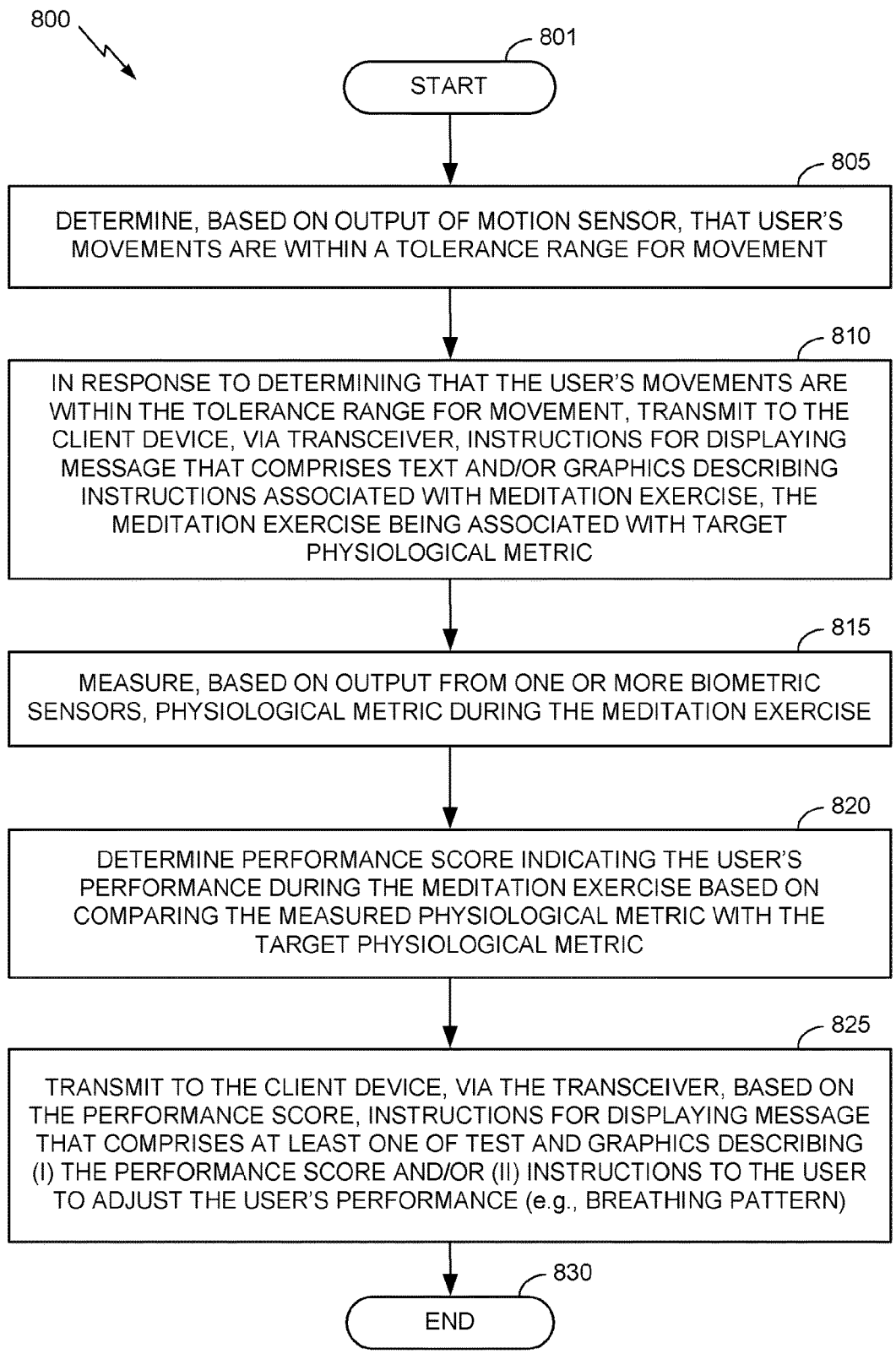
FIG. 10 is a flowchart illustrating another example method for providing biofeedback during a meditation exercise in accordance with aspects of this disclosure.

FIG. 10 is a flowchart illustrating another method for providing biofeedback during a meditation exercise in accordance with aspects of this disclosure. The steps of method 800 illustrated in FIG. 10 may be performed by a wearable device 10 or component(s) thereof. For example, the method 800 may be performed by a processor 120 of the wearable device 10. In another example, a client device 20 in communication with the wearable device 10 may perform at least some of the steps of the method 800. For convenience, method 800 is described as performed by the processor 120 of the wearable device 10.

In one implementation, the wearable device 10 comprises one or more biometric sensors 160 including a motion sensor 162, a transceiver 140, and the processor 120. The method begins at block 801. At block 805, the processor 120 determines, based on output of the motion sensor 162, that a user's movements are within a tolerance range for movement. At block 810, in response to determining that the user's movements are within the tolerance range for movement, the processor 120 transmits, via the transceiver 140, instructions to a client device 20 to display a message that comprises at least one of text and graphics describing instructions associated with a meditation exercise. The meditation exercise may comprise or be associated with a target physiological metric (e.g., a target respiration metric).

At block 815, the processor 120 measures, based on output of at least one of the one or more biometric sensors 160, a physiological metric (e.g., a respiration metric of the user's breathing pattern) during the meditation exercise. At block 820, the processor 120 determines a performance score indicating the user's performance during the meditation exercise based on comparing the measured physiological metric with the target physiological metric. At block 825, the processor 120 transmits, via the transceiver 140, based on the performance score, instructions to the client device 20 to display a message that comprises at least one of text and graphics. The text and graphics describing at least one of (i) the performance score and (ii) instructions to the user to adjust the user's performance (e.g., instructions to adjust the user's breathing pattern). The method 800 ends at block 830.

In accordance with various embodiments described herein, the meditation exercise may correspond to a breathing exercise. In such case, the measured physiological metric (e.g., see operations 715 in FIGS. 9 and 815 in FIG. 10) may correspond to a measured respiration metric of the user's breathing pattern, and the target physiological metric (e.g., see operations 710 in FIGS. 9 and 810 in FIG. 10) may correspond to a target respiration metric including a target breathing pattern. For example, in some embodiments, the respiration metric may relate to one or more of (i) user breathing rate, (ii) user inhalation timing, depth, and/or duration, (iii) user exhalation timing, depth, and/or duration, and (iv) a consistency and/or variability of one or more of (i), (ii), and (iii). More information regarding such respirations metrics is described in more detail below.

In some embodiments, the meditation exercise may correspond to a motion-based exercise, such as where the user is instructed to maintain position or otherwise stay still/ stationary for a period of time. In such case, the measured physiological metric may quantify how still the user remains during portions of the meditation exercise. For example, the measured physiological metric (e.g., see operations 715 in FIGS. 9 and 815 in FIG. 10) may correspond to a measured level of activity, movement, or motion of the user during a time period (e.g., as measured by the motion sensor 162 of wearable device 10), and the target physiological metric (e.g., see operations 710 in FIGS. 9 and 810 in FIG. 10) may correspond to a maximum threshold level or a threshold range of activity, movement, or motion of the user during a time period.

In some embodiments, the meditation exercise includes a heart rate related component (e.g., as measured while the user is instructed to stay still and/or follow a breathing pattern). In such case, the measured physiological metric (e.g., see operations 715 in FIGS. 9 and 815 in FIG. 10) reflects parameters of the user's heart rate (e.g., as measured by the optical sensor 300 of wearable device 10) during the meditation exercise comprising one or more of (i) average heart rate, (ii) minimum heart rate, (iii) maximum heart rate and/or (iv) change of heart rate during the exercise (e.g., as quantified by metrics such as heart rate variability, periodicity, randomness, spectral energy). The target physiological metric (e.g., see operations 710 in FIGS. 9 and 810 in FIG. 10) may correspond to target values for the aforementioned parameters of the user's heart rate.

The physiological metric, as described herein, may also be referred to as a relaxation metric, a meditation metric, a calmness metric, a stress-relief metric, or an activity metric.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

What is claimed is:

1. A method of operating a wearable device, the wearable device comprising a processor, one or more biometric sensors and a graphical user interface, the biometric sensors including a motion sensor and an optical biometric sensor configured to detect features of a user's cardiac signal, the method comprising:

determining, via the processor based on output of the motion sensor, that the user's movements are within a tolerance range for movement;

prompting the user, via the graphical user interface, to perform a meditation exercise in response to the determining that the user's movements are within the tolerance range for movement, the meditation exercise being associated with a target physiological metric related to the physiology of the user;

measuring, based on output of at least the optical biometric sensor, a physiological metric of the user during the meditation exercise, wherein the tolerance range for movement includes one or more values defined such that changes in the physiological metric are due to the meditation exercise rather than the user's movement;

determining, via the processor, a performance score indicating the user's performance during the meditation exercise based on comparing the measured physiological metric with the target physiological metric; and providing, via the graphical user interface, based on the performance score, feedback information indicative of the user's performance during the meditation exercise the feedback information being provided to the user concurrently with the prompting of the user to perform the meditation exercise.

2. The method in claim 1, wherein the physiological metric of the user is associated with one or more of the user's heart rate, and the user's respiration.

3. The method in claim 2, wherein the physiological metric associated with the user's heart rate measures parameters of the user's heart rate during the meditation exercise comprising one or more of (i) average heart rate, (ii) minimum heart rate, (iii) maximum heart rate, and/or (iv) change of heart rate during the exercise.

4. The method of claim 2, wherein the physiological metric associated with the user's respiration corresponds to a respiration metric of the user's breathing pattern, and wherein measuring the respiration metric comprises monitoring one or more of: (i) user breathing rate; (ii) user inhalation timing, depth, and/or duration; (iii) user exhalation timing, depth, and/or duration; and (iv) a consistency and/or variability of one or more of (i), (ii), and (iii).

5. The method of claim 4, wherein:
the prompting of the user to perform the meditation exercise comprises displaying, via the graphical user interface, instructions regarding the target physiological metric, the target physiological metric corresponding to a target respiration metric including a target user breathing pattern;
the measuring of the respiration metric comprises measuring a current user breathing pattern; and
the determining of the performance score comprises comparing the current user breathing pattern to the target user breathing pattern.

6. The method of claim 4, further comprising:
determining a baseline respiration metric based on an output from at least one the optical biometric sensor received prior to prompting the user to perform the meditation exercise,
wherein the determining of the performance score is further based on comparing the measured respiration metric to the baseline respiration metric.

7. The method of claim 1, wherein:
the determining of the performance score comprises determining the performance score during a first part of the meditation exercise;

the method further comprises generating, based on the performance score during the first part of the meditation exercise, instructions to the user to adjust the user's performance; and the providing of the feedback information comprises providing, via the graphical user interface, the generated instructions during a second part of the meditation exercise.

8. The method of claim 1, wherein the wearable device further comprises at least one of a display, a light-emitting circuit, a sound-producing circuit, and a haptic drive circuit.

9. The method of claim 8, wherein the prompting of the user comprises rendering a message on the display, wherein the message comprises at least one of text and graphics describing instructions associated with the meditation exercise.

10. The method of claim 8, wherein the providing of the feedback information comprises rendering a message on the display, wherein the message comprises at least one of text and graphics describing at least one of (i) the performance score and (ii) instructions to the user to adjust the user's performance.

11. The method of claim 1, wherein the wearable device further comprises a transceiver configured to communicate with a client device.

12. The method of claim 11, wherein the client device comprises one of a personal computer, a mobile phone, and a tablet computing device.

13. The method of claim 11, further comprising wirelessly transmitting, via the transceiver, instructions to the client device to display a message that comprises at least one of text and graphics describing instructions associated with the meditation exercise.

14. The method of claim 11, further comprising wirelessly transmitting, via the transceiver, instructions to the client device to display a message that comprises at least one of text and graphics describing at least one of (i) the performance score and (ii) instructions to the user to adjust the user's performance.

15. The method of claim 1, further comprising:
measuring, based on the output of at least the optical biometric sensor, a second physiological metric of the user; and
selecting the meditation exercise for the user based on the measured second physiological metric.

16. The method of claim 15, wherein the measured second physiological metric comprises at least one of: user heart rate; user photoplethysmography (PPG); user blood pressure; user respiration rate; user skin conduction; user blood glucose levels; user blood oxygenation; user skin temperature; user body temperature, user electromyography; and user electroencephalography (EEG).

17. The method of claim 15, wherein:
the wearable device comprises a memory circuit; and
the meditation exercise is selected from among a set of defined meditation exercises stored in the memory circuit based on at least one of (i) the measured second physiological metric and (ii) a user performance score from a previous meditation exercise.

18. The method of claim 1, wherein providing the feedback information comprises providing a visual image representative of the performance score.

19. The method of claim 1, wherein the method further comprises:
determining, based on the output of the motion sensor, that the user's movements are not within the tolerance range for movement;

in response to determining that the user's movements are not within the tolerance range, delaying at least one of (i) the prompting of the user to perform the meditation exercise and (ii) the measuring of the physiological metric of the user.

20. The method of claim 1, further comprising:
measuring, based on output of a heart rate monitor, the user's heart rate variability; and
determining a change in the user's heart rate variability based on comparing (i) a first heart rate variability measurement before commencement of the meditation exercise and (ii) a second heart rate variability measurement after the commencement of the meditation exercise,
wherein the determining of the performance score is further based on the change in the user's heart rate variability.

21. The method of claim 1, further comprising:
measuring, based on the output of at least the optical biometric sensor, a second physiological metric of the user; and
determining that the measured second physiological metric is outside a defined tolerance range for the second physiological metric,
wherein the prompting of the user to perform the meditation exercise is further in response to the determining that the second physiological metric is outside the defined tolerance range for the second physiological metric.

22. A method of operating a wearable device, the wearable device comprising a processor, one or more biometric sensors and a wireless communication transceiver, the biometric sensors including a motion sensor and an optical biometric sensor configured to detect features of a user's cardiac signal, the method comprising:
determining, via the processor based on output of the motion sensor, that the user's movements are within a tolerance range for movement;
in response to determining that the user's movements are within the tolerance range for movement, transmitting to a client device including a graphical user interface, via the transceiver, instructions for displaying a message via the graphical user interface that comprises at least one of text and graphics describing instructions associated with a meditation exercise, the meditation exercise being associated with a target physiological metric related to the physiology of the user;
measuring, based on output of at least the optical biometric sensor, a physiological metric of the user during the meditation exercise, wherein the tolerance range for movement includes one or more values defined such that changes in the physiological metric are due to the meditation exercise rather than the user's movement;
determining, via the processor, a performance score indicating the user's performance during the meditation exercise based on comparing the measured physiological metric with the target physiological metric; and
transmitting to the client device, via the transceiver, based on the performance score, instructions for displaying a message on the graphical user interface that comprises at least one of text and graphics describing at least one of (i) the performance score and (ii) instructions to the user to adjust the user's performance, the message being provided to the user concurrently with the prompting of the user to perform the meditation exercise.

23. The method of claim 22, wherein the client device comprises one of a personal computer, a mobile phone, and a tablet computing device.

24. A wearable device, comprising:
one or more biometric sensors including a motion sensor and an optical biometric sensor configured to detect features of a user's cardiac signal;
a graphical user interface;
at least one processor; and
a memory storing computer-executable instructions for controlling the at least one processor to:
determine, via the at least one processor based on output of the motion sensor, that the user's movements are within a tolerance range for movement;
prompt the user, via the graphical user interface, to perform a meditation exercise in response to determining that the user's movements are within the tolerance range for movement, the meditation exercise being associated with a target physiological metric related to the physiology of the user;
measure, based on output of at least the optical biometric sensor, a physiological metric of the user during the meditation exercise, wherein the tolerance range for movement includes one or more values defined such that changes in the physiological metric are due to the meditation exercise rather than the user's movement;
determine, via the at least one processor, a performance score indicating the user's performance during the meditation exercise based on comparing the measured physiological metric with the target physiological metric; and
provide, via the graphical user interface, based on the performance score, feedback information indicative of the user's performance during the meditation exercise, the feedback information being provided to the user concurrently with the prompting of the user to perform the meditation exercise.

25. The device of claim 24, wherein the memory further comprises computer-executable instructions for controlling the at least one processor to:
determine the performance score by determining the performance score during a first part of the meditation exercise;
generate, based on the performance score during the first part of the meditation exercise, instructions to the user to adjust the user's performance; and
provide the feedback information by instructing the graphical user interface to display the generated instructions during a second part of the meditation exercise.

26. The device of claim 24, wherein the device further comprises at least one of a display, a light-emitting circuit, a sound-producing circuit, and a haptic drive circuit.

27. The device of claim 24, wherein the memory further comprises computer-executable instructions for controlling the at least one processor to:
prompt the user to perform the meditation exercise by displaying, via the graphical user interface, instructions regarding the target physiological metric, the target physiological metric corresponding to a target respiration metric including a target user breathing pattern;
measure the physiological metric by measuring a current user breathing pattern; and
determine the performance score by comparing the current user breathing pattern to the target user breathing pattern.

28. A wearable device, comprising:
one or more biometric sensors including a motion sensor and an optical biometric sensor configured to detect features of a user's cardiac signal;
a wireless communication transceiver;
at least one processor; and
a memory storing computer-executable instructions for controlling the at least one processor to:
- determine, via the at least one processor based on output of the motion sensor, that the user's movements are within a tolerance range for movement;
- in response to determining that the user's movements are within the tolerance range for movement, transmit to a client device comprising a graphical user interface, via the transceiver, instructions for displaying a message via the graphical user interface that comprises at least one of text and graphics describing instructions associated with a meditation exercise, the meditation exercise being associated with a target physiological metric related to the physiology of the user;
- measure, based on output of at least the optical biometric sensor, a physiological metric of the user during the meditation exercise, wherein the tolerance range for movement includes one or more values defined such that changes in the physiological metric are due to the meditation exercise rather than the user's movement;
- determine, via the at least one processor, a performance score indicating the user's performance during the meditation exercise based on comparing the measured physiological metric with the target physiological metric; and
- transmit to the client device, via the transceiver, based on the performance score, instructions for displaying a message via the graphical user interface that comprises at least one of text and graphics describing at least one of (i) the performance score and (ii) instructions to the user to adjust the user's performance, the message being provided to the user concurrently with the prompting of the user to perform the meditation exercise.

29. The device of claim 28, wherein the memory further comprises computer-executable instructions for controlling the at least one processor to:
- determine the performance score by determining the performance score during a first part of the meditation exercise;
- generate, based on the performance score during the first part of the meditation exercise, instructions to the user to adjust the user's performance; and
- instruct the transceiver to transmit the generated instructions to the client device to display the generated instructions during a second part of the meditation exercise.

* * * * *